(12) United States Patent
van de Berg et al.

(10) Patent No.: US 6,832,507 B1
(45) Date of Patent: Dec. 21, 2004

(54) SYSTEM FOR DETECTING THE PRESENCE OF MOISTURE

(75) Inventors: Jan van de Berg, Gouda (NL); Peter Hillebrand de Haan, Delft (NL)

(73) Assignee: Telesensing Holding B.V. (NL)

( * ) Notice: Subject to any disclaimer, the term of this patent is extended or adjusted under 35 U.S.C. 154(b) by 0 days.

(21) Appl. No.: 09/786,841

(22) PCT Filed: Sep. 10, 1999

(86) PCT No.: PCT/NL99/00562

§ 371 (c)(1),
(2), (4) Date: Sep. 19, 2001

(87) PCT Pub. No.: WO00/16081

PCT Pub. Date: Mar. 23, 2000

(30) Foreign Application Priority Data

Sep. 11, 1998 (NL) .............................. 1010067

(51) Int. Cl.$^7$ ................................. G01N 5/02
(52) U.S. Cl. ................. 73/73; 338/38; 338/34; 338/35; 324/668; 324/652; 324/712; 324/653; 324/664
(58) Field of Search .................... 73/73; 338/38, 338/34, 35; 324/668, 652, 712, 653, 664

(56) References Cited

U.S. PATENT DOCUMENTS

| | | | |
|---|---|---|---|
| 3,686,606 A | 8/1972 | Thoma et al. | |
| 4,272,718 A | * 6/1981 | Kashiuchi et al. | .......... 324/668 |
| 4,646,069 A | 2/1987 | Andrejasich et al. | |
| 4,929,885 A | * 5/1990 | Dishman | .................... 324/664 |

FOREIGN PATENT DOCUMENTS

| | | |
|---|---|---|
| DE | 26 55 271 A1 | 6/1978 |
| DE | 40 30 284 A1 | 6/1992 |
| EP | 0 329 436 | 8/1989 |
| GB | 2 192 059 A | 12/1987 |
| GB | 2 245 976 A | 1/1992 |
| WO | WO 84/01626 | 4/1984 |

\* cited by examiner

Primary Examiner—Hezron Williams
Assistant Examiner—André K. Jackson
(74) Attorney, Agent, or Firm—Muserlian, Lucas and Mercanti

(57) ABSTRACT

The system comprises at least one electronic sensor for detecting the presence of moisture. The system further comprises at least one reading device for obtaining information from the sensor about the presence of moisture. The sensor comprises a resonant circuit which is at least partly formed from a moisture sensitive material, the electrical resistance of which increases when the material comes into contact with moisture. The reading device comprises transmitter-receiver means for generating an elecromagnetic interrogation field.

19 Claims, 3 Drawing Sheets

SYSTEM FOR DETECTING THE PRESENCE OF MOISTURE

CROSS-REFERENCE TO RELATED APPLICATIONS

This patent application claims the benefit of priority from Dutch Patent Application No. NL 1010067 filed Sep. 11, 1998 through PCT Application Serial No. PCT/NL99/00562 filed Sep. 10, 1999, the contents of each of which are incorporated herein by reference.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

The invention relates to a system for detecting the presence of moisture, comprising at least one electronic sensor for detecting the presence of moisture and at least one reading device for obtaining information from the at least one sensor about the presence of moisture, wherein the at least one sensor comprises a resonant circuit which is at least partly formed from a moisture sensitive material, the electrical resistance of which changes when the material comes into contact with moisture, the reading device comprises means for generating an electromagnetic interrogation field comprising at least one frequency component corresponding to a resonance frequency of the resonant circuit and for recording the response of the at least one sensor to the electromagnetic interrogation field to obtain information about the presence of moisture at the at least one sensor.

Such a system is known from DE 40 30 284. In the known system, the reading device is provided with a measuring circuit comprising a transformer connected to the resonance circuit. The resonant circuit comprises a material from which the electrical resistance decreases when the material comes into contact with moisture.

It is a drawback of the known system that the information generated by the sensor about the presence of moisture is often not sufficiently reliable. Moreover, such a system is rather expensive and thus less suitable for use as a disposable sensor, because the reading device and the sensor are part of one and the same device. Furthermore the system is not suitable for wirelessly obtaining information about the presence of moisture.

The invention has for its object, inter aila, to meet the above drawbacks and, furthermore, to provide a number of advantages.

The system according to the invention is accordingly characterized in that the electrical resistance of the material (18) increases when the material comes in to contact with moisture and the reading device (4.1) comprising transmitter-receiver means (14) for wirelessly generating the electromagnetic interrogation field and for wirelessly recording the response of the at least one sensor (2.i) to the electromagnetic interrogation field to obtain the information about the presence of moisture at the at least one sensor (2.i). if the at least one sensor (2.i) is wirelessly brought into the electromagnetic interrogation field.

It has been found that the effect of moisture on the moisture sensitive material and thus the presence of moisture at the sensor can be recorded very sensitively and accurately. When the moisture sensitive material comes into contact with moisture, the electrical resistance will increase. Because of the increase in the electrical resistance, the electrical properties of the resonant circuit will change and the response of the resonant circuit to the interrogation field will thereby also change. In this connection it is even conceivable that in this manner not only the presence of moisture at the sensor is detected, but that even an impression can be obtained of the amount of moisture present at the sensor.

The sensor according to the invention can be used, inter alia, in baby diapers, incontinence diapers, sanitary towels, incubators, packages for vegetables and fruit, on the road surface for detection of rain and at a substratum in the cultivation under glass. It is also possible to use the sensor in drying processes, such as, for instance, in the paper industry.

GB 21 92 059 discloses a system comprising a wetness sensor for wirelessly reading the wetness sensor. The system is for measuring the moisture content of oil in a container. The wetness sensor comprises a moisture detector, an active transmitter and an antenna for generating a modulation of the transmission signal according to the resistance of the moisture detector by changing the q-factor of the antenna. In this known system energy is supplied to the sensor by means of mechanical vibration submitted to an outerwall of the container comprising the sensor.

EP-A-0 329 436 discloses a moisture and dew detection sensor comprising a fabric and a moisture sensing resistive substance adhered in a substantially continued and dispersed state to the fabric.

The resistance of the fabric increases if it comes into contact with moisture. Furthermore, the resistance of the fabric is measured by a non-wireless connection to a measuring unit. The system is, however, not provided with a reading unit which generates an interrogation field with a frequency which corresponds with a resonance frequency of a resonance circuit of the sensor so that the resonance circuit is brought to resonance by means of the interrogation field.

Preferably, it applies that the moisture sensitive material is included in the resonant circuit in such a manner that the Q factor of the resonant circuit decreases when the resistance of the moisture sensitive material increases. The Q factor of the intact dry sensor is therefore high. This means that the sensor can be properly detected in this condition. The system can therefore also be used to check whether a sensor is present in the product (such as, for instance, a diaper). This possibility is not present at the above prior art sensor, because this sensor does not react when no short circuit is present between the two electrodes.

A further advantage is that the change in the characteristic of the sensor is reversible. When the sensor dries again, the resistance of the moisture sensitive material will decrease.

In the above special embodiment this means that the Q factor of the resonant circuit increases again.

According to a special embodiment it applies that the resonant circuit at least comprises an LC circuit. In this connection the entire LC circuit or at least part of the LC circuit may be built up from the moisture sensitive material In particular, it applies that the moisture sensitive material comprises a binding agent capable of swelling in moisture, in which binding agent electrically conductive particles are included. It is also possible that the moisture sensitive material comprises a binding agent in which particles capable of swelling in moisture and electrically conductive particles are included. In both cases moisture ensures a swelling of respectively the binding agent and the particles capable of swelling. Consequently, the electrically conductive particles will be drawn apart and the conductivity of the moisture sensitive material will decrease so that the electrical resistance of the material increases.

In particular, it applies that the reading device generates an alarm signal when moisture is detected by means of the sensor.

According to a very advanced embodiment of the invention the system is also designed as an identification system in which the at least one sensor comprises an active electronic circuit connected with the resonant circuit, such as a microprocessor in which an identification code is stored, which identification code is passed to the resonant circuit when the resonant circuit is resonated by the electromagnetic interrogation field, and the reading device being arranged to read the identification code by means of the electromagnetic interrogation field.

This system can, for instance, advantageously be used in a hospital, the sensor being used to record moisture in a mattress of a hospital bed. Each sensor may then comprise an identification code belonging to a specific hospital bed. In this manner it is not only possible to record that a mattress has become wet, but also which mattress has become wet.

The system may further comprise a central control unit which is, optionally wirelessly, connected with the at least one reading device for obtaining information about the presence of moisture at the at least one sensor.

In the example of the above hospital the central control unit can be installed, for instance, in the room of a nurse. The reading devices can be installed in the different rooms of the patients. In this manner it can be centrally recorded in which room which bed has got a wet mattress.

The invention will now be explained in more detail with reference to the drawing, in which:

FIG. 4a shows a second alternative embodiment of a sensor of the system of FIG. 1;

FIG. 4b shows an electrical equivalent circuit diagram of the sensor of FIG. 4a;

Figure 5A:
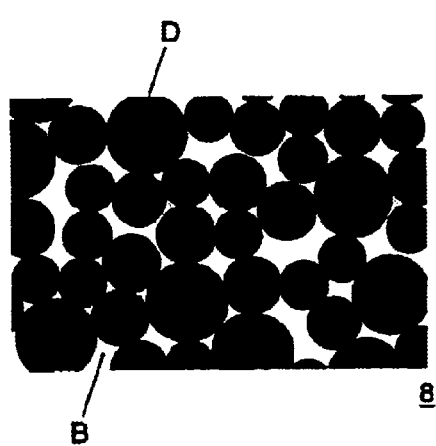
Figure 5B:
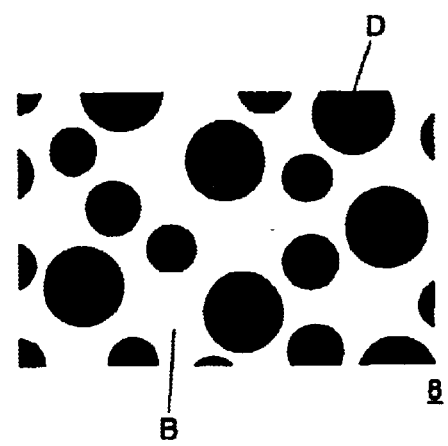

FIG. 5a diagrammatically shows a relatively dry condition of the moisture sensitive material of one of the sensors of FIGS. 1, 3, 4a and 4b; and FIG. 5b shows the moisture sensitive material of FIG. 5a, when this is relatively moist.

Figure 1:
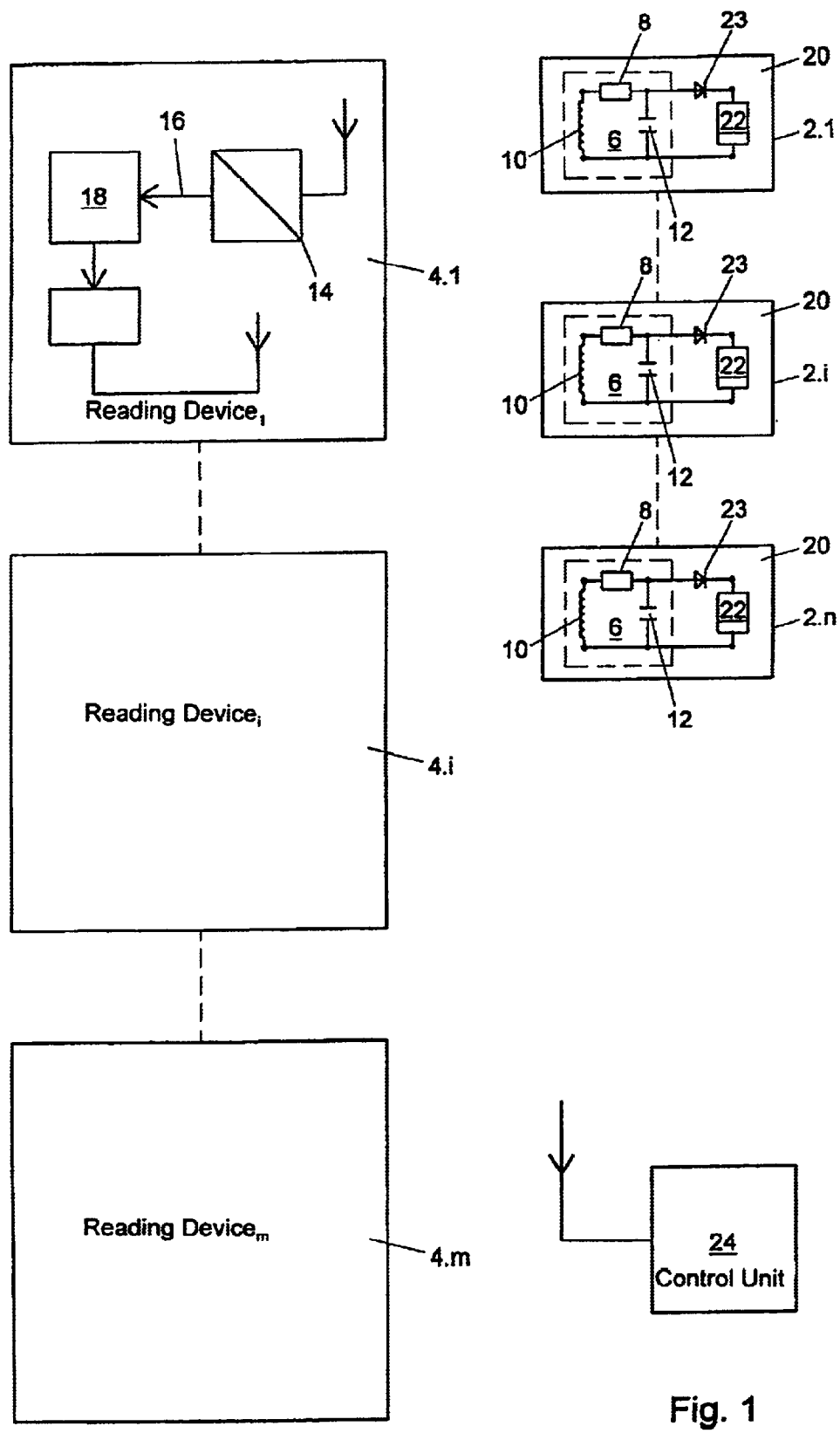
FIG. 1 shows a possible embodiment of a system for detecting the presence of moisture according to the invention.

In FIG. 1 a system for detecting the presence of moisture is indicated by reference numeral 1. The system comprises a number of electronic sensors 2.i (i=1, 2, . . . , n) for detecting the presence of moisture. The system further comprises at least one reading device 4.1 for obtaining information from the sensors 2.i about the presence of moisture.

Each of the sensors 2.i comprises a resonant circuit 6 shown in dotted lines, which is at least partly formed from a moisture sensitive material 8. In this example the resonant circuit comprises an LC circuit 10, 12, in which the moisture sensitive material 8 is included. The moisture sensitive material is of a type of which the electrical resistance increases when the material comes into contact with moisture.

The reading device 4.1 comprises transmitting and receiving means 14 for generating an electromagnetic interrogation field. The electromagnetic interrogation field comprises at least one frequency component which corresponds to a resonance frequency of the resonant circuit 6. In this example the resonant circuit has only one resonance frequency $f_0$. The electromagnetic interrogation field then also has one frequency $f_0$. It is explicitly observed that it is also possible that the electromagnetic interrogation field comprises more frequencies, for instance, because it can be shifted in frequency.

The operation of the apparatus is as follows. To check whether moisture is present at the sensor 2.i, the electromagnetic interrogation field is transmitted by means of transmitter-receiver unit 14 at the frequency $f_0$. When the sensor is not moist, this means that the resistance of the moisture sensitive material 8 is low. This means that the Q factor of the LC circuit is high. When the resonant circuit is therefore brought into the interrogation field, the resonant circuit will start to resonate and therefore to vibrate at the frequency $f_0$. By means of the transmitter-receiver unit 14 it is recorded that the resonant circuit 6 is in vibration. The information about the presence of moisture at sensor 2.i thus wirelessly obtained by the transmitter-receiver unit 14 is passed via line 16 of the reading device 4.1 to a signal processing unit 18 of the reading device.

The signal processing unit 18 may, for instance, comprise a threshold circuit to determine whether the response of the resonant circuit 6 is above or below a specific value. If the response is above this specific value, then it can be concluded that the sensor is dry, and if the response is below this predetermined value, then it can be concluded that the sensor is wet. In that case an alarm signal 19 can be generated by the signal processing unit 18 in a known per se manner.

The moisture sensitive material 8 can be applied in different manners. Thus, for instance, the sensor 2.i can be composed of a sheet-like carrier material 20, layers of conductive material forming the resonant circuit 6 being applied by known per se techniques. In this example this resonant circuit comprises, inter alia, a coil 10 and a capacitor 12. The coil 10 and the capacitor 12 can each be made of, for instance, copper. The moisture sensitive material 8 can be arranged on the carrier material 20 as a separate resistor. Both the coil 10 and the capacitor 12 and the moisture sensitive resistor 8 are arranged in the form of traces.

Figures 4A, 4B:
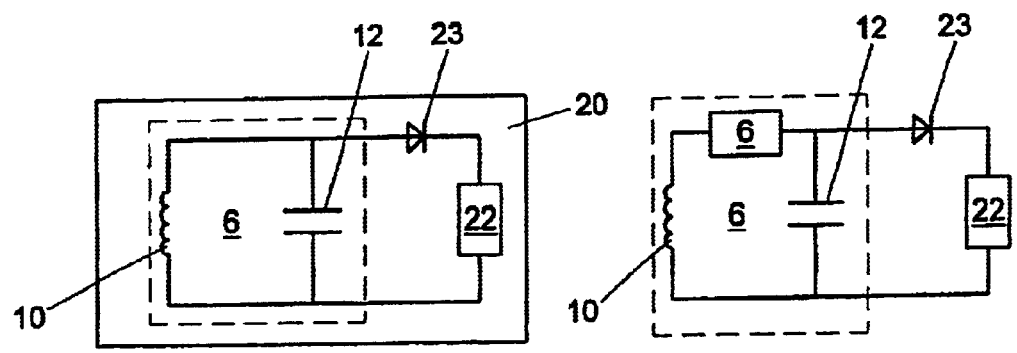

It is also possible that the material of the LC circuit itself is made of moisture sensitive material. Such a resonant circuit is shown in FIG. 4a. In FIG. 4a at least part of the coil 10 and/or the capacitor 12 is therefore made of the moisture sensitive material.

FIG. 4b shows the electrical equivalent circuit diagram thereof, which therefore corresponds to the diagram of the sensor shown in FIG. 1.

The realization of the moisture dependent conductivity of the moisture sensitive material can be obtained, for instance, by mixing electrically conductive particles D, preferably silver-containing, with a binding agent B capable of swelling in water, in such a manner that the particles D make a continuous contact, that is to say that the concentration of the particles rises above the percolation limit (see also FIG. 5a). The layer thickness of the thus formed conductive coating 8 can be of the order of what, for instance, can be applied with screen printing (10–500 µm). By contact with water the binding agent B will swell so that the electrically conductive particles are driven apart and the continuous contact is broken. That is to say that the concentration of the particles D falls below the percolation limit (see FIG. 5b).

Instead of a binding agent capable of swelling in water, particles capable of swelling in water can also be used in combination with the electrically conductive particles, while the employed binding agent itself need not be capable of swelling in water, but is water-sensitive to a greater or less degree. The nature and concentration of the particles capable of swelling as well as the nature and concentration of the binding agent are parameters adapted to adjust the velocity and degree of swelling. A specific characteristic of the material with respect to moisture can thus be obtained. Two examples of recipes for water-sensitive electrically conductive materials are:

EXAMPLE 1

Stabilizer (0.5% in water) 50 water 10 glycerine (10% in water) 1.25 metallite silver SF 20 2.5

NaOH (10% in water) 0.25

Layer thickness wet 500 µm

Layer thickness dry 100 µm

Response time <1 s

EXAMPLE 2

PA 18 polyanhydride resin (40% in MEK) 1.00

Stabileze (activated in $NH_3$), particles <60 µm 0.25 glycerine (20% in butanol) 1.00 metalite silver SF 20 1.50

MEK/butanol (1/1) 2.00 layer thickness wet: 300 µm layer thickness dry: 170 µm response time: ca. 45 s

As conductive particles different material types and forms of can be chosen. Examples are metals such as silver, copper, rvs, aluminum and zinc in forms like granules, fibers, flakes, globules etc. Also materials such as soot, graphite or intrinsically conductive polymer particles can be used in principle.

By properly composing the moisture sensitive coating material the moisture sensor can be made with standard coating and printing techniques like screen printing, ball printing, roller coating, spray coating etc.

As stated, the moisture sensitive material 8 can be included in the resonant circuit in such a manner that the Q factor of the resonant circuit decreases when the resistance of the moisture sensitive material increases.

Figure 2:
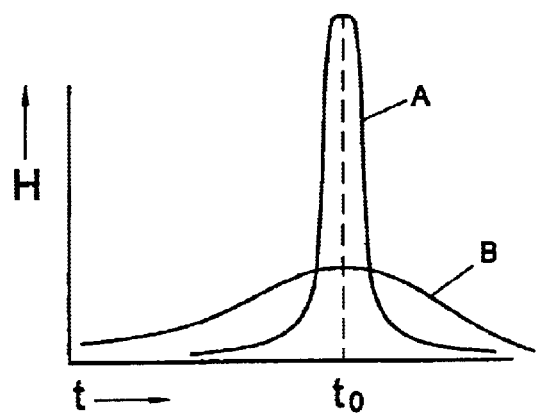
FIG. 2 shows the transfer characteristic of a resonant circuit of a sensor of the system of FIG. 1.

In FIG. 2 curve A indicates the transfer function H of the resonant circuit 6 when the moisture sensitive material is dry, that is to say when the Q factor is high. Then B indicates the curve obtained when the moisture sensitive material is wet, which has the result that the Q factor decreases.

The transmitter-receiver means 14 can be designed as a transmission system for detecting an electromagnetic response signal generated by the sensor 2.$i$, in response to the electromagnetic interrogation field. In fact, when the resonant circuit is vibrated by the electromagnetic interrogation field, it will therefore transmit an electromagnetic response signal which can in turn be detected by the transmitter-receiver means 14. This is referred to as a known per se transmission system. The signal processing device 18 can determine, by means of the intensity of the detected response signal, to what extent the sensor 2.$i$ is in contact with moisture. For the above sensor, in which the Q factor decreases when the sensor comes into contact with water, the signal processing device 18 may comprise a threshold circuit to determine whether the detected intensity is below a predetermined value. If it is actually below a predetermined value, then it can be concluded that the sensor 2.$i$ is wet and, if desired, an alarm signal 19 can be produced.

It is also possible, however, that the transmitter-receiver unit is designed as a known per se absorption system. When the resonant circuit 6 is vibrated by the electromagnetic interrogation field, this energy will absorb from the electromagnetic interrogation field. This energy absorption can be detected in the transmitter-receiver unit 14 in a known per se manner. When the sensor is dry and therefore has a high Q factor, much energy will be taken up from the interrogation field. On the other hand, when the sensor is moist, little or no energy will be taken up from the interrogation field.

Via line 16, information can again be supplied to the signal processing device 18 in the form of the amount of energy absorbed from the electromagnetic interrogation field. The reading device 4.1 can then determine on the basis of the amount of energy absorbed by the at least one sensor to what extent the at least one sensor is in contact with moisture. In particular, the signal processing device 18 comprises a threshold circuit to determine whether the amount of energy absorbed is below a predetermined value.

Preferably, it applies that each sensor 2.$i$ further comprises an active electronic circuit, such as a microprocessor 22 in which an identification code belonging to the sensor 2.$i$ is stored. The microprocessor is connected with the resonant circuit 6. When the resonant circuit is in the interrogation field, a part of the currents generated in the resonant circuit can be rectified by means of, for instance, a diode 23 and supplied to the microprocessor 22. In reaction to this, the microprocessor will supply the stored identification codes to the resonant circuit. The response signal generated in the resonant circuit in response to the electromagnetic interrogation field is then modulated by means of the identification code. This identification code can be detected by the transmitter-receiver unit 14 and supplied to the signal processing unit 18. The signal processing unit 18 can then determine from which sensor 2.$i$ a response has been detected. Such a system is highly important when it comprises, as in the present example, a plurality of sensors 2.$i$. When at a given moment the response of one or more sensors falls away, because the sensor in question comes into contact with moisture, it can be established by means of the reading device 4.1 which identification code is no longer received and, therefore, which sensor is in contact with moisture.

Such a system can advantageously be used in a hospital in which each mattress comprises a sensor 2.$i$. When one of the mattresses then becomes moist, this can be detected by means of the reading device 4.1, and moreover, it can be established which sensor and, therefore, which mattress is concerned. The nurse can then start changing the patient, if required.

The system can further be extended with a central control unit 24 and a plurality of reading devices 4.$i$ ($i$=1, 2, ..., m). Each reading device 4.$i$ is optionally wirelessly connected with the central control unit 24 to obtain information about the presence of moisture at one of the sensors 2.$i$. In use, a reading device 4.$i$ can be installed, for instance, in each room of a hospital. Furthermore, a number of beds with mattresses are installed in each room, each of which mattresses comprises a sensor 2.$i$ with a specific identification code. When one of the mattresses in the rooms becomes moist, an alarm signal can thus be generated at the central control unit 24, so that a nurse can immediately establish which sensor has come into contact with moisture.

Figure 3:
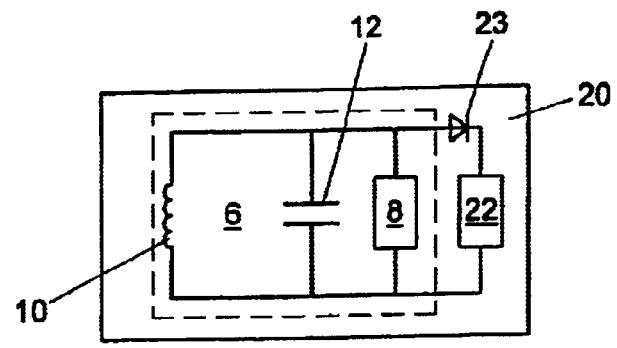
FIG. 3 shows a first alternative embodiment of a sensor of the system of FIG. 1.

The invention is by no means limited to the above embodiments. Thus, for instance, the moisture sensitive material 8 can also be included in the resonant circuit in such a manner that the Q factor of the resonant circuit increases when the resistance of the moisture sensitive material increases. An example thereof is shown in FIG. 3. In this example the moisture sensitive material 8 is parallel-connected to the LC circuit 10, 12 in the form of a resistor. When the sensor of FIG. 3 is dry, the resistance of the moisture sensitive material 8 will be low and thus in fact cause a short circuit in the LC circuit 10, 12. This means that the sensor of FIG. 3 will hardly, if at all, react to the interrogation field when the sensor is dry. On the other hand, when the sensor comes into contact with moisture, the resistance of the moisture sensitive material will increase and the short circuit will gradually be removed. This has the result that in this case the LC circuit will react when brought into the above interrogation field. This reaction can then be detected by means of the reading device, both when the reading device is designed as a transmission system and as an absorption system. When, therefore, an electromagnetic response signal is received, when it is detected that energy is taken up from the electric interrogation field, it can be concluded that the sensor in question is wet.

In the example of FIG. 3, the sensor comprises the microprocessor discussed above. When the sensor of FIG. 3 reacts, the identification code can then also be sent directly to the transmitter-receiver device, so that by means of the reading device it can be directly established which sensor reacts, in other words, which sensor is wet or moist. The transfer of the resonant circuit of FIG. 3 is therefore, such that curve A of FIG. 2 is applicable when the sensor is wet and curve B when the sensor is dry. It is also conceivable that each sensor 2.$i$ comprises a resonant circuit with a unique resonance frequent $f_i$, with $f_i \neq t_j$ if i≠j. By emitting, i.e., generating or propagating, an interrogation field, the frequency of which increases in a previously known manner, it can be detected whether a sensor 2.$i$ is moist, while at the same time the frequency $f_i$ and thus the identity of a sensor can be established.

It is further also conceivable that other principles are used, so that the electrical resistance of the material of the LC circuit is changed. By way of example, it can be mentioned that the electrical resistance of the intrinsically conductive polymers, such as polyaniline, polypyrrole or polythiophene, changes under the influence of water in which salts or ions are included. In that case, in particular for instance, urine can be detected. It is explicitly mentioned that in each of the embodiments the microprocessor can be left out.

Such variants are each deemed to fall within the scope of the invention.

What is claimed is:

1. A system with at least one sensor for detecting the presence of moisture, comprising:
    a resonant circuit having a resonance frequency and being at least partly formed from a moisture sensitive material having an electrical resistance which increases when in contact with moisture, comprising:
    a) transmitter-receiver means for generating an electromagnetic interrogation field comprising at least one frequency component corresponding to the resonance frequency of said resonance circuit and being structured and arranged relative to said at least one sensor such that the electromagnetic interrogation field generated by said transmitter-receiver means is wirelessly propagated;
    b) said at least one sensor being arranged to be wirelessly activated by said electromagnetic interrogation field when present in the electromagnetic interrogation field to generate a response to the electromagnetic interrogation field;
    c) said transmitter-receiver means being structured and arranged relative to said at least one sensor such that said response of said at least one sensor about the presence of moisture, is wirelessly received by said transmitter-receiver means, and
    d) a reading device comprising said transmitter-receiver means for recording said response of said at least one sensor to the electromagnetic interrogation field to obtain information about the presence of moisture at said at least one sensor.

2. A system according to claim 1, wherein said moisture sensitive material is included in said resonant circuit such that the Q factor of said resonant circuit decreases when the resistance of said moisture sensitive material increases.

3. A system according to claim 1, wherein said moisture sensitive material is included in said resonant circuit such that the Q factor of said resonant circuit increases when the resistance of said moisture sensitive material increases.

4. A system according to claim 1, wherein said resonant circuit comprises an LC circuit.

5. A system according to claim 4, wherein at least a portion of said LC circuit is made from the moisture sensitive material.

6. A system according to claim 1, wherein the moisture sensitive material comprises a binding agent including particles capable of swelling in moisture and electrically conductive particles.

7. A system according to claim 1, wherein the moisture sensitive material comprises a binding agent capable of swelling in moisture and containing electrically conductive particles.

8. A system according to claim 1, wherein the moisture sensitive material is arranged on a carrier material in the form of a coating.

9. A system according to claim 4, wherein at least part of the LC circuit is formed by a coating.

10. A system according to claim 1, wherein said transmitter-receiver device is designed as a transmission system for detecting an electromagnetic response signal generated by said at least one sensor in response to the electromagnetic interrogation field.

11. A system according to claim 10, wherein said at least one reading device determines on the basis of the intensity of the detected response signal to what extent said at least one sensor is in contact with moisture.

12. A system according to claim 2, wherein said at least one reading device comprises a threshold circuit arranged to determine whether the detected intensity is below a predetermined value.

13. A system according to claim 1, wherein said transmitter-receiver device is designed as an absorption system for detecting energy absorbed from the interrogation field by said at least one sensor in response to the electromagnetic interrogation field.

14. A system according to claim 13, wherein said at least one reading device determines on the basis of the amount of energy absorbed by said at least one sensor the extent to which said at least one sensor is in contract with moisture.

15. A system according to claim 2, wherein said at least one reading device comprises a threshold circuit arranged to determine whether the amount of energy absorbed is below a predetermined value.

16. A system according to claim 1, wherein said at least one reading device generates an alarm signal when moisture is detected by means of said at least one sensor.

17. A system according to claim 1, wherein said at least one sensor comprises a microprocessor connected with the resonant circuit and in which an identification code is stored, which identification code is passes to the resonant circuit when the resonant circuit is resonated by the electromagnetic interrogation field, and said at least one reading device being arranged to read the identification code by means of the electromagnetic interrogation field.

18. A system according to claim 1, the system further comprises a central control unit which is, wirelessly, connected with said at least one reading device for obtaining information about the presence of moisture at said at least one sensor.

19. A system according to claim 4, wherein the entirety of said LC circuit is made from the moisture sensitive material.

* * * * *